United States Patent
Hirata et al.

(10) Patent No.: US 9,188,576 B2
(45) Date of Patent: Nov. 17, 2015

(54) GAS SENSOR

(71) Applicant: NGK INSULATORS, LTD., Nagoya-shi, Aichi (JP)

(72) Inventors: Shodai Hirata, Nagoya (JP); Takehiro Koganei, Nagoya (JP); Nobukazu Ikoma, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 0 days.

(21) Appl. No.: 14/225,602

(22) Filed: Mar. 26, 2014

(65) Prior Publication Data
US 2014/0290333 A1 Oct. 2, 2014

(30) Foreign Application Priority Data

Mar. 29, 2013 (JP) ................ 2013-071828

(51) Int. Cl.
G01N 33/00 (2006.01)
G01N 27/407 (2006.01)

(52) U.S. Cl.
CPC ........ G01N 33/0009 (2013.01); G01N 27/4078 (2013.01); G01N 33/0037 (2013.01)

(58) Field of Classification Search
CPC .................. G01N 33/0009; G01N 27/4078
See application file for complete search history.

(56) References Cited

U.S. PATENT DOCUMENTS

| 5,874,663 A | 2/1999 | Fukaya et al. |
| 2002/0003088 A1 | 1/2002 | Ozawa |

FOREIGN PATENT DOCUMENTS

| DE | 10338462 | | 3/2005 |
| JP | 9-196885 | A | 7/1997 |
| JP | 11-190716 | A | 7/1999 |
| JP | 11-190717 | A | 7/1999 |
| JP | 2000-81412 | A | 3/2000 |
| JP | 2000-97900 | A | 4/2000 |
| JP | 2004-198360 | A | 7/2004 |
| JP | 2004-212156 | A | 7/2004 |
| JP | 2004-226117 | A | 8/2004 |
| JP | 2004-279267 | A | 10/2004 |

OTHER PUBLICATIONS

Extended European Search Report for the corresponding European patent application No. 14162291.0 issued on Jun. 23, 2014.
The Japanese Office Action for the corresponding Japanese patent application No. 2013-071828 issued on Sep. 8, 2015.

*Primary Examiner* — Laura Martin
*Assistant Examiner* — Alex Devito
(74) *Attorney, Agent, or Firm* — Global IP Counselors, LLP (57) ABSTRACT

An outer tube and a rubber plug are swaged at two sites, a first swaged section located on the side of connections between contact fittings of a connector and leads and a swaged section located closer to an open end of the outer tube than the first swaged section, such that the inside diameter of a portion of the outer tube is greater than the inside diameter. This prevents reduction of the detection accuracy of a gas sensor because sealing properties can be enhanced by heavily swaging at the second swaged section than the first swaged section. Additionally, excessive force can be prevented on the connections and the leads by lightly swaging the first swaged section rather than the second swaged section. Thus, the disconnection between the connector and the leads can be prevented.

4 Claims, 5 Drawing Sheets

GAS SENSOR

CROSS-REFERENCE TO RELATED APPLICATIONS

This application claims priority to Japanese Patent Application No. 2013-071828 filed in Japan on Mar. 29, 2013, the contents of which are hereby incorporated herein by reference.

BACKGROUND

1. Field of the Invention

The present invention relates to a gas sensor.

2. Description of the Related Art

Hitherto, there have been known gas sensors for detecting the concentration of a predetermined substance, such as $NO_x$, in measured gas such as an automobile exhaust gas. For example, Japanese Unexamined Patent Application Publication No. 09-196885 describes a gas sensor including a sensor element which is placed in a tubular body made of metal and which detects the concentration of gas at the tip of the tubular body, a connector in contact with an electrode placed on the back end side of the sensor element, an elastic body (grommet) attached to a back open end of the tubular body, and a lead which is connected to the connector and which extends outward from an open end of the tubular body through a through-hole of the elastic body. In the gas sensor, two sites spaced at a predetermined distance in an axial direction of the tubular body are swaged, whereby the elastic body is fixed to the tubular body by multi-stage (two-stage) swaging.

SUMMARY

In such a gas sensor, in order to ensure sealing properties of an elastic body to enhance the detection accuracy of the concentration of gas, the elastic body and a tubular body need to be sufficiently swaged. However, if excessive force is applied to the elastic body by swaging, then a connection between a connector and a lead is misaligned and therefore electrical connectivity may possibly be adversely affected.

It is a main object of a gas sensor according to the present invention to ensure better sealing properties and electrical connectivity in the case of sealing an open end of a tubular body enclosing a sensor element by swaging an elastic body.

In order to achieve the above main object, the gas sensor according to the present invention has taken means below.

The present invention provides a gas sensor including a sensor element capable of detecting the concentration of measured gas, a connector electrically connected to the sensor element, a tubular body in which the sensor element and the connector are placed and which has an open end, leads which are connected to the connector and which extend outward from the open end of the tubular body, and an elastic body which is placed in the tubular body so as to seal the open end, in which connections between the connector and the leads are placed, and through which the leads extend, the tubular body and the elastic body are radially swaged at a plurality of swaged sections including a first swaged section located on the connection side and a second swaged section located closer to the open end than the first swaged section, and the inside diameter of a portion of the tubular body that corresponds to the first swaged section is greater than the inside diameter of a portion of the tubular body that corresponds to the second swaged section.

In the gas sensor according to the present invention, the tubular body, which has the open end, and the elastic body, in which the connections between the connector and the leads are placed and through which the leads extend, are radially swaged at the swaged sections, which includes the first swaged section located on the connection side and the second swaged section located closer to the open end than the first swaged section, and the inside diameter of the portion of the tubular body that corresponds to the first swaged section is greater than the inside diameter of the portion of the tubular body that corresponds to the second swaged section. This allows the second swaged section to be more enhanced in sealing properties (sealing ability) of the elastic body than the first swaged section to prevent leaks. In the first swaged section, excessive force can be prevented from acting on the connections between the connector and the leads or the leads extending through the elastic body and therefore the disconnection between the connector and the leads can be prevented from occurring. Thus, better sealing properties and electrical connectivity are ensured, whereby the reduction in detection accuracy of the gas sensor can be prevented.

Herein, "the swaged section located on the connection side" may be one containing a site where at least the connections are placed is swaged, one which is swaged so as to entirely surround the connections, or one which is swaged so as to partly surround the connections. The expression "the inside diameter of a portion of the tubular body that corresponds to the first swaged section is greater than the inside diameter of a portion of the tubular body that corresponds to the second swaged section" is equivalent to the expression "the outside diameter of a portion of the elastic body that corresponds to the first swaged section is greater than the outside diameter of a portion of the elastic body that corresponds to the second swaged section" because the tubular body and the elastic body are usually swaged together. In the first and second swaged sections, when the thickness and outside diameter of the unswaged tubular body are the same, "the outside diameter of the portion of the tubular body that corresponds to the first swaged section is greater than the outside diameter of the portion of the tubular body that corresponds to the second swaged section".

In the gas sensor according to the present invention, the inside diameter of the portion of the tubular body that corresponds to the first swaged section may be 1% to 5% greater than the inside diameter of the portion of the tubular body that corresponds to the second swaged section. This allows, in the first swaged section, sealing properties of the elastic body to be prevented from being significantly impaired and also allows excessive force to be prevented from acting on the connections between the connector and the leads.

In the gas sensor according to the present invention, the swaging ratio determined by dividing the difference in inside diameter between the portion of the tubular body before swaging that corresponds to the second swaged section and the portion of the tubular body after swaging that corresponds to the second swaged section by the inside diameter of the tubular body before swaging may be within the range of 8% to 14%. This allows adverse effects caused by excessively swaging the second swaged section to be reduced and also allows sufficient sealing properties to be ensured. Herein, when the inside diameter of the tubular body before swaging is known, the inside diameter thereof may be used as "the inside diameter of the tubular body before swaging". Alternatively, the inside diameter of an unswaged portion of a region accommodating the elastic body of the tubular body after swaging may be used as "the inside diameter of the tubular body before swaging". If, for example, a non-swaged portion is present between the first and second swaged sections, then the inside diameter of the non-swaged portion may be used as "the inside diameter of the tubular body before swaging".

In the gas sensor according to the present invention, the elastic body may contain an inorganic filler. This allows the elastic body to have increased hardness and drawback; hence, sealing properties can be maintained for a long period.

DETAILED DESCRIPTION OF THE EMBODIMENTS

Embodiments of the present invention will now be described with reference to the attached drawings.

Figure 1:
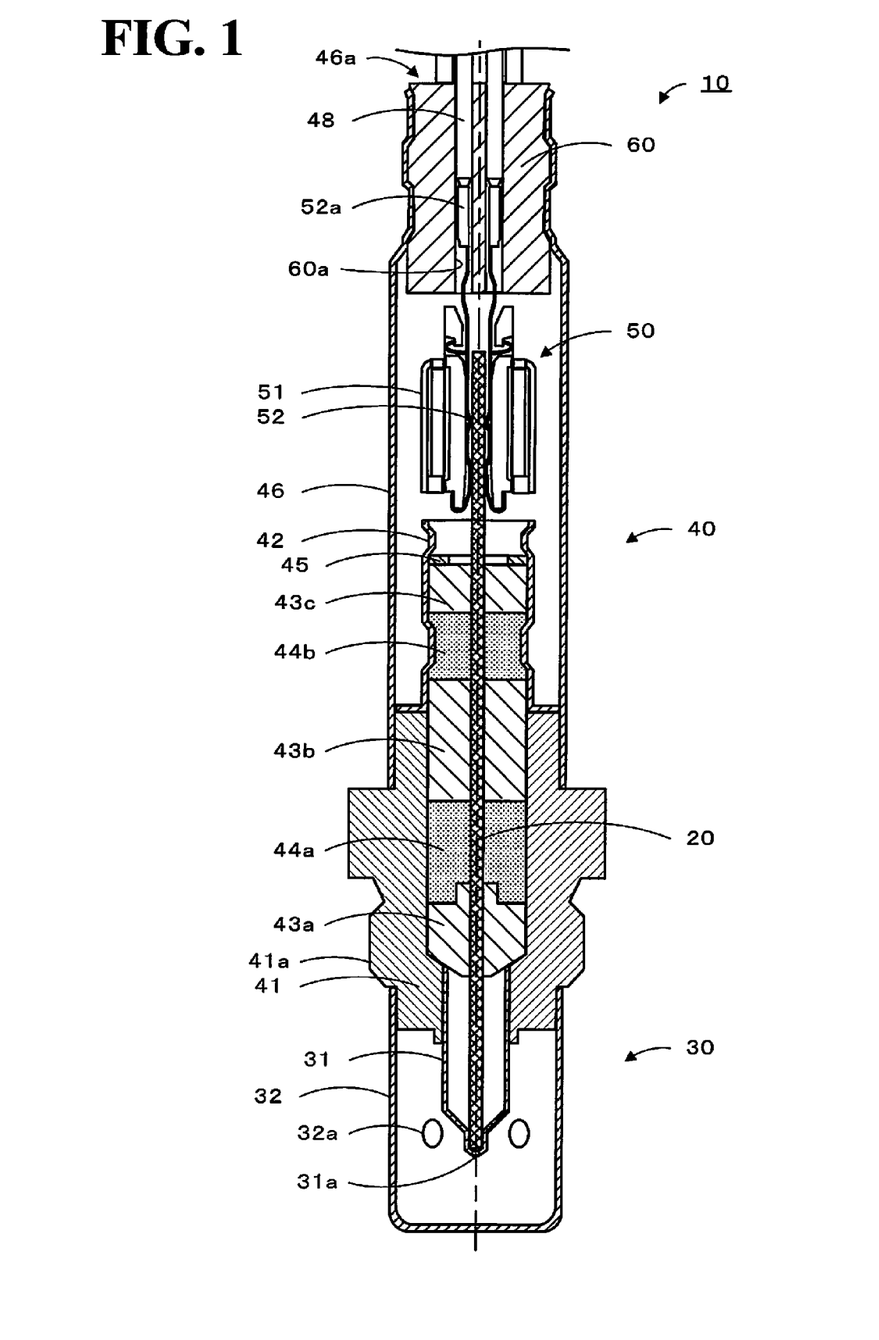
FIG. 1 is a sectional view of a gas sensor 10 according to an embodiment of the present invention.

FIG. 1 is a sectional view of a gas sensor 10 according to an embodiment of the present invention. As shown in FIG. 1, the gas sensor 10 includes a sensor element 20 for measuring the concentration of a predetermined gas component in measured gas, a protective cover 30 protecting an end portion of the sensor element 20, and a sensor assembly 40 including a rubber plug 60 and a connector 50 electrically connected to the sensor element 20. The gas sensor 10 is attached to, for example, a vehicle's exhaust pipe and used to measure the concentration of a substance, such as $NO_x$ or $O_2$, contained in an exhaust gas which is measured gas.

The sensor element 20 is an element with a narrow elongated plate-like shape and is composed of, for example, six stacked ceramic substrates each including an oxygen-ion conducting solid electrolyte layer made of zirconia ($ZrO_2$) or the like. Herein, an end portion of the sensor element 20 that is located on the protective cover 30 side is referred to as a free end and an end portion of the sensor element 20 that is located on the connector 50 is referred to as a base end. The front and back surfaces of the base end of the sensor element 20 each have electrodes (not shown) for applying a voltage to the sensor element 20 or extracting the electromotive force or current generated depending on the concentration of a gas component detected by the sensor element 20. The electrodes are arranged on the front and back surfaces of the sensor element 20 and are electrically connected to an electrode (not shown) placed in the free end of the sensor element 20 through a conducting path extending in the sensor element 20.

The protective cover 30 is placed so as to surround the periphery of the free end of the sensor element 20. The protective cover 30 includes an inner protective sub-cover 31 covering the free end of the sensor element 20 and an outer protective sub-cover 32 covering the inner protective sub-cover 31. The inner protective sub-cover 31 is tube-shaped and has an inner protective cover hole 31a for introducing measured gas to the free end of the sensor element 20. The outer protective sub-cover 32 has a bottomed cylindrical shape and also has, placed in the side surface, outer protective cover holes 32a for introducing measured gas. The inner protective sub-cover 31 and the outer protective sub-cover 32 are made of, for example, metal such as stainless steel.

The sensor assembly 40 includes a main fitting 41 made of metal, a cylindrical inner tube 42 welded to the main fitting 41, a cylindrical outer tube 46 welded to the main fitting 41, the connector 50, the rubber plug 60. The connector 50 is connected to the base end of the sensor element 20. The rubber plug 60 is attached to the outer tube 46. The main fitting 41 is attachable to, for example, automotive exhaust pipes using a male screw portion 41a. The following members are enclosed in the main fitting 41 and the inner tube 42: a plurality of ceramic supporters 43a to 43c and ceramic powders 44a and 44b such as talc powders. The ceramic powder 44a is placed between the ceramic supporters 43a and 43b and the ceramic powder 44b is placed between the ceramic supporters 43b and 43c. The ceramic supporters 43a to 43c and the ceramic powders 44a and 44b are surrounded by a metal ring 45, the inner wall of the main fitting 41, and the inner wall of the inner tube 42 and are thereby sealed. The outer tube 46 covers surroundings of the inner tube 42, the sensor element 20, and the connector 50 and has an open end 46a (the upper end of the outer tube 46 shown in FIG. 1). The rubber plug 60 is attached to the open end 46a.

The connector 50 includes a housing 51 made of a ceramic such as sintered alumina and contact fittings 52 which are supported by the housing 51 and which are in contact with the electrodes of the sensor element 20. The contact fittings 52 extend outside the connector 50 and are electrically connected to leads 48 through connections 52a which are crimp contacts. In the connector 50, the number (for example, four, eight, or the like) of the contact fittings 52 corresponds to the number of the electrodes placed on the front and back surfaces of the sensor element 20. Therefore, the number of the connections 52a is more than one (for example, four, eight, or the like) and the number of the leads 48 is also more than one (for example, four, eight, or the like).

The rubber plug 60 is located at the open end 46a of the outer tube 46; is a member, made of fluoro-rubber, for sealing gaps between the outer tube 46 and the leads 48 (the connections 52a); and has through-holes 60a extending therein. The connections 52a are placed in the through-holes 60a and the leads 48 are inserted in the through-holes 60a. The plurality of through-holes are provided to accommodate the plurality of connections 52a and leads 48. Since the gas sensor 10 is attached to a vehicle's exhaust pipe, the gas sensor 10 needs to be compact due to a limitation in installation space. Therefore, the connections 52a are placed in the through-holes 60a, whereby the length (length in axial direction) of the rubber plug 60 is limited and the gas sensor 10 is made compact (the length of the outer tube 46 is limited). The rubber plug 60 contains a filler (aggregate) made of an inorganic material. The filler is an alumina ($Al_2O_3$) or silica ($SiO_2$) powder with a particle size of 0.1 μm to 10 μm and the content of the filler is 1% to 30% by weight. The use of the filler allows the rubber plug 60 to have increased hardness.

Figure 2:
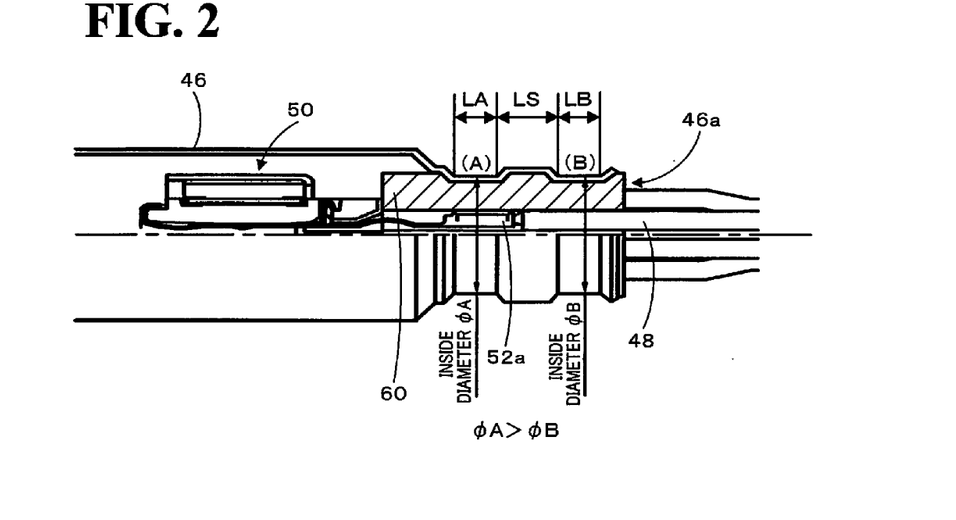
FIG. 2 is a sectional view of swaged sections of the gas sensor 10.

The rubber plug 60 is radially swaged together with the outer tube 46 and is thereby fixed in the outer tube 46. FIG. 2 shows swaged sections thereof in cross section. As shown in FIG. 2, two swaged sections are arranged in an axial direction of the outer tube 46 (the rubber plug 60): one located on the connector 50 side (the sensor element 20 side) is referred to as a swaged section A ((A) in FIG. 2) and the other located closer to the open end 46a than the swaged section A (on the side on which the leads 48 extend outward) is referred to as a swaged section B ((B) in FIG. 2). The swaged section A is one formed by swaging the entire periphery of the outer tube 46 at sites (sites which correspond to the connections 52a in a radial direction of the outer tube 46 and which are located directly above and under the connections 52a as shown in FIG. 2) corresponding to the connections 52a between the contact fittings 52 and the leads 48. The swaging width LA (the length in the axial direction of the outer tube 46) of the swaged section A is within the width (within the length in the axial direction of the outer tube 46 at the connections 52a) of the connections 52a. The swaged section B is apart from the swaged section A at a predetermined distance LS and has a swaging width LB equal to the swaging width LA. When the inside diameter of a portion of the outer tube 46 that corresponds to the swaged section A and the inside diameter of a portion of the outer tube 46 that corresponds to the swaged section B are expressed as inside diameter φA and inside diameter φB, respectively, the relation "inside diameter φA>inside diameter φB" holds. That is, the swaged section B is one more heavily swaged than the swaged section A. In this embodiment, in the swaged sections A and B, the inside diameter and thickness of the unswaged outer tube 46 are invariant and therefore inside diameter φA and inside diameter φB correspond to the outside diameter of the swaged rubber plug 60.

The rubber plug 60 is used to the seal the open end 46a of the outer tube 46. Therefore, if the rubber plug 60 is not sufficiently swaged, then sealing properties are not ensured and moisture and gases other than measured gas leak into the outer tube 46 to adversely affect the detection accuracy of the sensor element 20 in some cases. On the other hand, the leads 48 are inserted in the rubber plug 60 and the connections 52a between the contact fittings 52 and the leads 48 are placed in the rubber plug 60. Therefore, if the whole of the rubber plug 60 is excessively swaged, then excessive force acts on the leads 48 and the connections 52a. When excessive force acts on the leads 48 and the connections 52a, the leads 48 are likely to be broken, the resistance of the leads 48 becomes unstable, the connections 52a become faulty, and/or the contact of the connections 52a cause shorts; hence, electrical connectivity may possibly be impaired. Alternatively, if a site corresponding to the swaged section A is not swaged, then the connections 52a are not secured in the through-holes 60a and therefore the misalignment of the connections 52a (the contact fittings 52) is likely to be caused by vibrations from vehicles. Hence, in this case, electrical connectivity may possibly be impaired. Therefore, in this embodiment, the swaged section B is more heavily swaged than the swaged section A, whereby sealing properties are ensured and leaking is prevented. Since the swaged section A is more lightly swaged than the swaged section B, excessive force is prevented from acting on the connections 52a with the connections 52a secured and good electrical connectivity is achieved. The reason why the inside diameter φA of the swaged section A and the inside diameter φB of the swaged section B are set such that the relation "inside diameter φA>inside diameter φB" holds is that the prevention of leaking and the prevention of electrical connection failure are both achieved.

In the swaged section B, in order to ensure sealing properties, the swaging ratio is within the range of 8% to 14%, the swaging ratio being determined by dividing the difference (inside diameter before swaging−inside diameter φB after swaging) in inside diameter between the unswaged outer tube 46 and the swaged outer tube 46 by the inside diameter of the unswaged outer tube 46. The inside diameter of the portion of the unswaged outer tube 46 that corresponds to the swaged section B, is used as the inside diameter before swaging. Instead, the inside diameter of a portion (an unswaged portion located between the swaged sections A and B) of the swaged outer tube 46, the portion corresponding to the predetermined distance LS, may be used. Furthermore, in the swaged section A, the inside diameter φA is set to be slightly greater than the inside diameter φB such that swaging is slight and sealing properties are not significantly impaired. In particular, the inside diameter variance determined by dividing the difference between the inside diameter φA and the inside diameter φB by the inside diameter φB is 1% to 5%. That is, the inside diameter φA is 1% to 5% greater than the inside diameter φB. Furthermore, in this embodiment, since the hardness of the rubber plug 60 is increased by adding the filler to as described above, the durability of the rubber plug 60 can be increased. Therefore, the breakage of the rubber plug 60 can be reduced and obtained sealing properties can be maintained for a long period. In particular, the effect of adding the filler is significant because the gas sensor 10 is one used in vehicles and the rubber plug 60 is exposed to gas at a high temperature of higher than 250° C. and therefore is in a degradable environment.

A method for manufacturing the gas sensor 10 is described below. First, the main fitting 41 and the inner tube 42 are assembled by welding so as to be coaxial with each other. After the ceramic supporter 43a, the ceramic powder 44a, the ceramic supporter 43b, the ceramic powder 44b, and the ceramic supporter 43c are provided in the inner tube 42 in that order from the main fitting 41, the metal ring 45 is inserted in the inner tube 42. Next, the sensor element 20 is passed through the ceramic supporter 43c, the ceramic powder 44b, the ceramic supporter 43b, the ceramic powder 44a, and the ceramic supporter 43a in that order from the metal ring 45. The ceramic supporters 43a to 43c, the ceramic powders 44a and 44b, and the metal ring 45 each have a hole through which the sensor element 20 can be passed. The metal ring 45 and the main fitting 41 are pressed in a direction in which the metal ring 45 and the main fitting 41 approach each other, whereby the ceramic powders 44a and 44b are compressed. In such a state, a portion (an upper portion in FIG. 1) of the inner tube 42 that is located outside the metal ring 45 is reduced in diameter by swaging and a portion of the inner tube 42 that contains the ceramic powder 44b is also reduced in diameter by swaging, a primary assembly including the main fitting 41 and the sensor element 20 is obtained.

Figure 3:
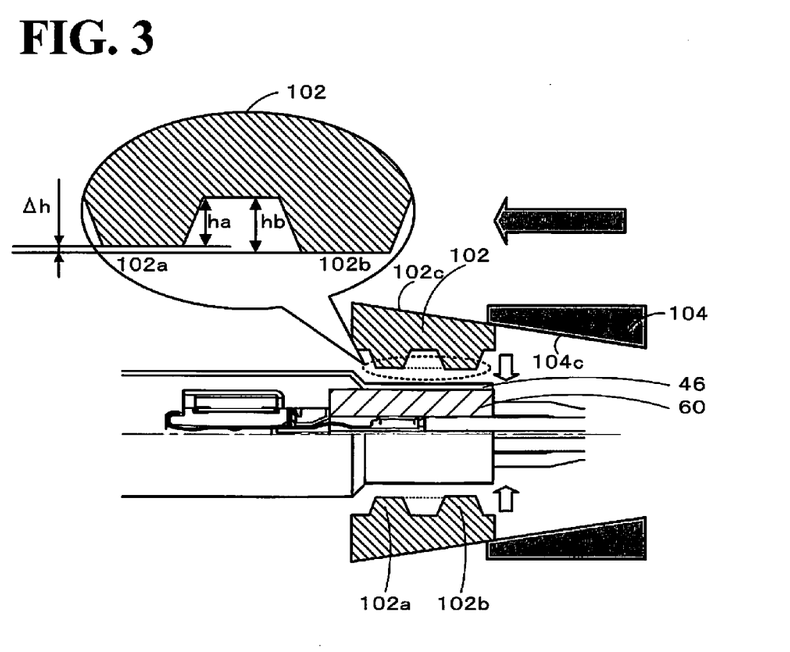
FIG. 3 is an illustration showing how an outer tube 46 and a rubber plug 60 are swaged in the course of manufacturing the gas sensor 10.
Figure 4A:
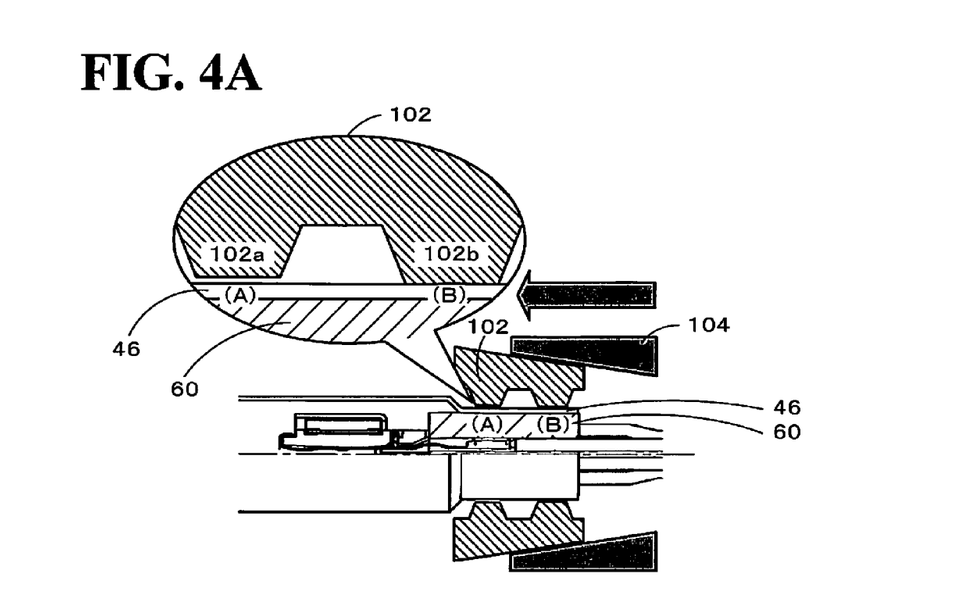
FIGS. 4A and 4B are illustrations showing how the outer tube 46 and the rubber plug 60 are swaged in the course of manufacturing the gas sensor 10.
Figure 4B:
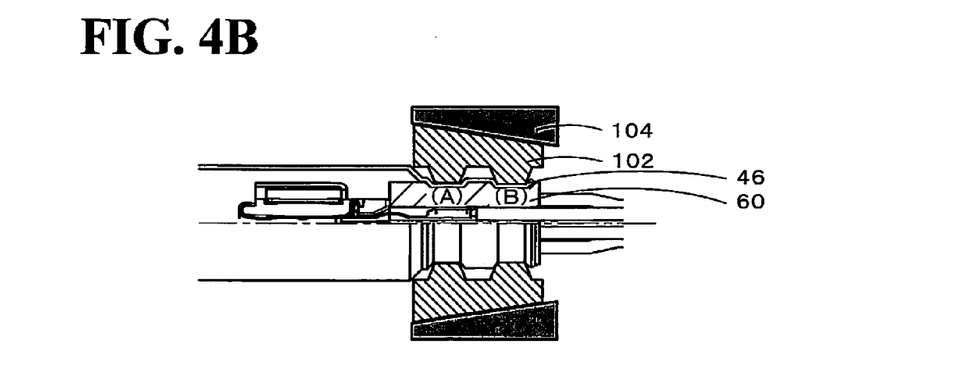

After the primary assembly is obtained as described above, the inner protective sub-cover 31 and the outer protective sub-cover 32 are welded to the main fitting 41, whereby the protective cover 30 is formed. The outer tube 46 is welded to the main fitting 41. Subsequently, the rubber plug 60 having the through-holes 60a is prepared. Herein, a rubber material for the rubber plug 60 is prepared in such a way that the filler, which is the alumina ($Al_2O_3$) with a particle size of 0.1 μm to 10 μm, is added to a rubber component such as fluoro-rubber such that the content thereof is 1% to 30% by weight, followed by kneading with a mixer or the like. The filler is not limited to the alumina ($Al_2O_3$) and may be a silica ($SiO_2$). The rubber material, prepared as described above, containing the filler is shaped so as to have a necessary form and size and is subjected to a step necessary to form the through-holes 60a, whereby the rubber plug 60 is obtained. The leads 48 are passed through the through-holes 60a of the rubber plug 60 and the connections 52a of the contact fittings 52 are connected to the leads 48, whereby the connector 50 is prepared. The connector 50 is connected to the base end of the sensor element 20. The rubber plug 60 is inserted in the open end 46a of the outer tube 46. Next, the outer tube 46 and the rubber plug 60 are reduced in diameter by swaging, whereby the rubber plug 60 is fixed to the outer tube 46. FIGS. 3 and 4 show how the outer tube 46 and the rubber plug 60 are swaged in the course of manufacturing the gas sensor 10.

As shown in FIG. 3, swaging is performed using swaging tools 102 set to a swaging machine (not shown) and a pressing tool 104 pressing the back side of the swaging tools 102. The swaging tools 102 each include a bump 102a for swaging the swaged section A and a bump 102b for swaging the swaged section B. As shown in an enlarged view in FIG. 3, the height ha of the bump 102a is slightly different from the height hb of the bump 102b. The height hb is greater than the height ha by Δh (for example, 0.1 mm, 0.2 mm, or the like). The swaging tools 102 have such a form that a cylindrical member is divided into eight pieces at 45°. Therefore, in the case where eight of the swaging tools 102 are set to the swaging machine so as to direct the bumps 102a and 102b inward and the gas sensor 10 is set to the center surrounded by the swaging tools 102, the swaging tools 102 are arranged around the outer tube 46, which is cylindrical. An outside back surface 102c of each swaging tool 102 and an inside pressing surface 104a of the pressing tool 104 are tapered at substantially the same angle. Therefore, when the pressing tool 104 moves leftward to bring the pressing surface 104a into contact with the back surface 102c as shown in FIG. 3, the swaging tool 102 (the bumps 102a and 102b) are pressed by the pressing tool 104 and therefore move substantially in parallel from outside toward the center side (the outer tube 46 side).

When the pressing tool 104 further moves leftward from a state shown in FIG. 3 and the swaging tool 102 move to the center side to abut the outer tube 46, swaging starts (refer to FIG. 4A). Since the height ha of the bump 102a and the height hb of the bump 102b are slightly different from each other, the bump 102b abuts the outer tube 46 prior to the bump 102a as shown in an enlarged view in FIG. 4A. That is, the bump 102b starts swaging prior to the bump 102a. Therefore, the swaged section B begins to be swaged prior to the swaged section A. The pressing tool 104 further moves leftward and therefore the swaging tool 102 are moved (pressed) toward the center side (the outer tube 46 side), whereby swaging is performed. When the pressing tool 104 reaches a predetermined position, swaging ends (refer to FIG. 4B). Herein, since the height hb is greater than the height ha by Δh, the bump 102b is greater in indentation depth than the bump 102a. Therefore, the bump 102b is greater in swaging depth than the bump 102a; hence, the inside diameter φB of the swaged section B is less than the inside diameter φA of the swaged section A. The gas sensor 10 in FIG. 1 is obtained by such a manufacturing method including swaging.

Figure 5A:
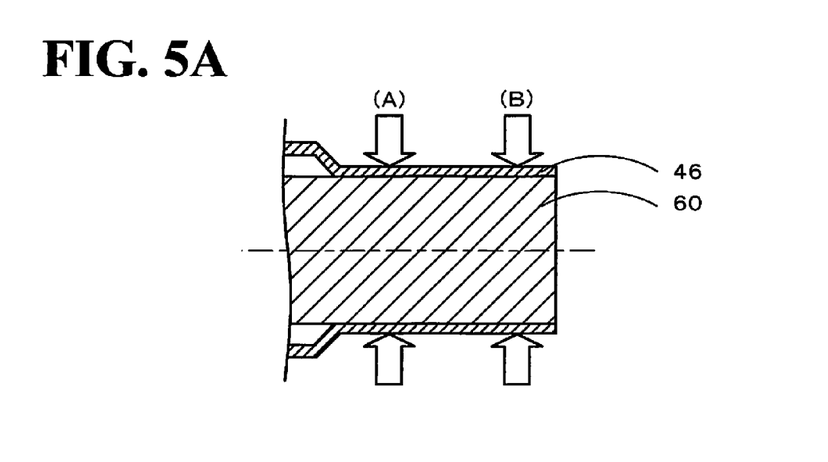
FIGS. 5A to 5C are illustrations showing how two swaged sections begin to be simultaneously swaged.
Figure 5B:
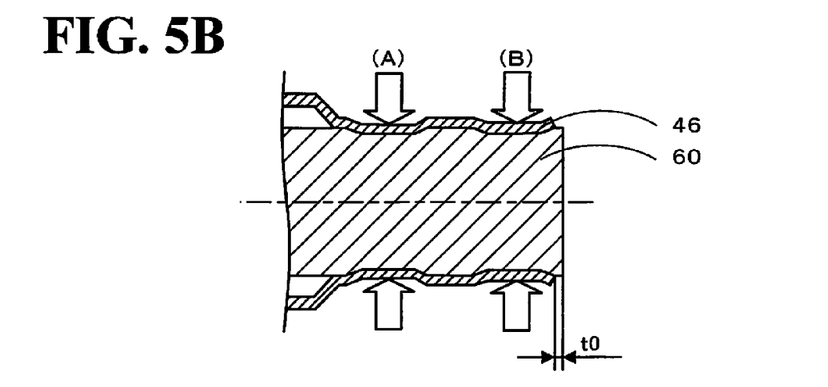
Figure 5C:
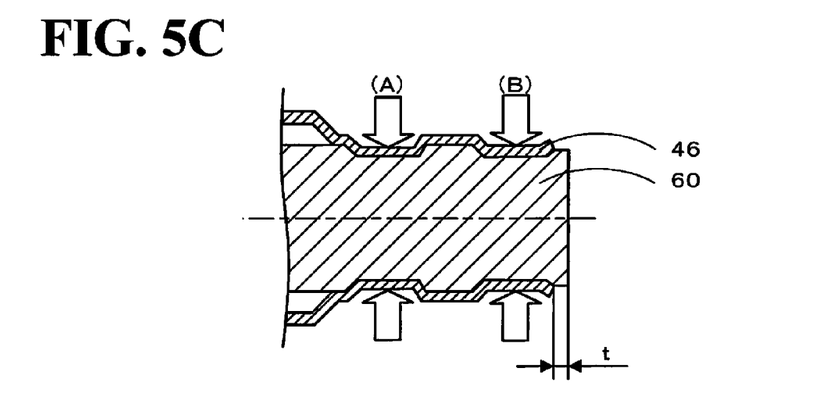
Figure 6A:
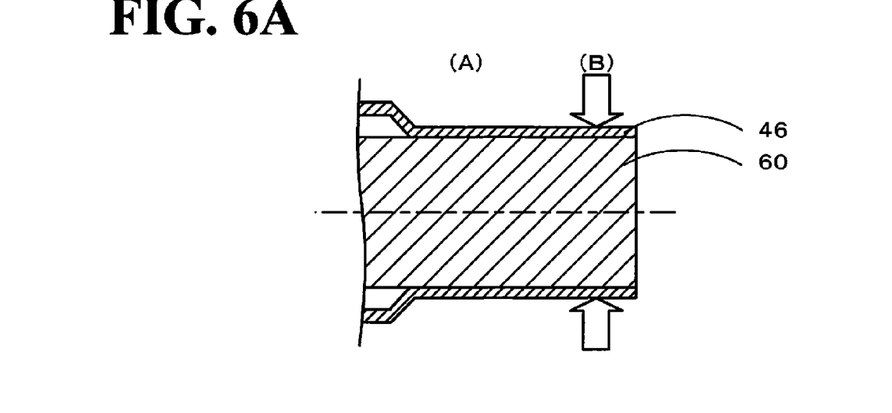
FIGS. 6A to 6C are illustrations showing how one of two swaged sections that is located on the open end side begin to be primarily swaged.
Figure 6B:
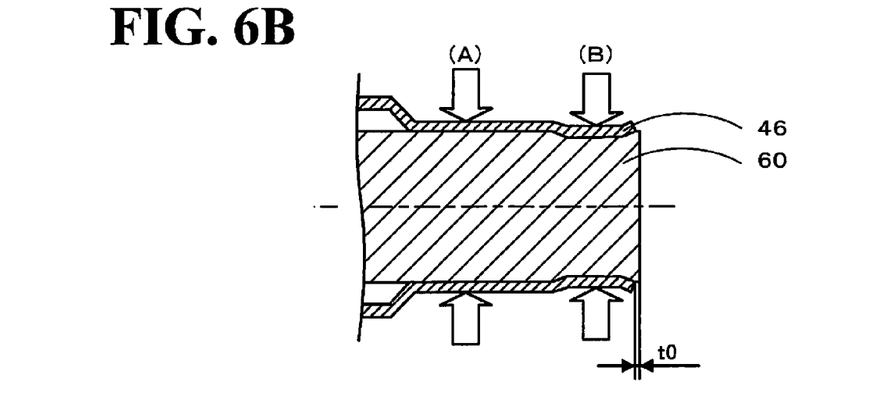
Figure 6C:
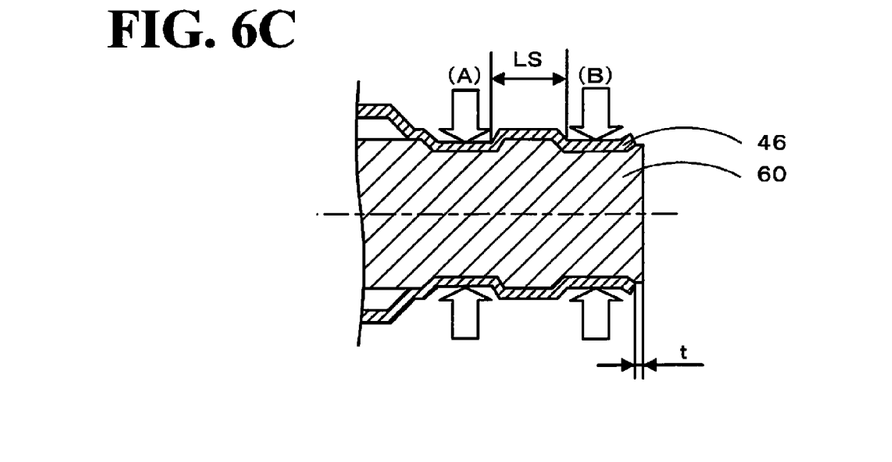

As described above, in the method for manufacturing the gas sensor 10, among the two swaged sections A and B, the swaged section B begins to be primarily swaged in the course of swaging the outer tube 46 and rubber plug 60. For comparison, FIGS. 5A to 5C show how two swaged sections begin to be simultaneously swaged. FIGS. 6A to 6C show how one of two swaged sections that is located on the open end side begins to be primarily swaged like this embodiment. In FIGS. 5A to 5C and 6A to 6C, the leads 48, the connections 52a, the through-holes 60a, or the like are not shown. As shown in FIGS. 5A to 5C, since the two swaged sections A and B begin to be simultaneously swaged (FIG. 5A), relatively strong force acts on the rubber plug 60 in a free state. Also, the elongation of rubber between (inside) the swaged sections A and B repels (inside elongation is restricted) and therefore rubber is likely to extend outward. That is, in the swaged section A, the rubber plug 60 relatively significantly extends leftward, and in the swaged section B, the rubber plug 60 relatively significantly extends rightward (in a direction in which the rubber plug 60 protrudes from the outer tube 46). Therefore, the projection length t0 of the rubber plug 60 protruding from the outer tube 46 is relatively large (FIG. 5B). The progression of swaging increases the elongation of the rubber plug 60 and also increases the projection length t of the rubber plug 60 protruding from the outer tube 46 (FIG. 5C). The connector 50, which is not shown, is present on the left side in FIGS. 5A to 5B and therefore the leftward elongation of the rubber plug 60 is more likely to be restricted as compared to the rightward elongation thereof. On the other hand, as shown in FIGS. 6A to 6C, among the two swaged sections A and B, the swaged section B is located on the open end side and begins to be primarily swaged (FIG. 6A); hence, the force acting on the rubber plug 60 at the start of swaging is less as compared to a comparative example and the leftward (inward) elongation of rubber in the swaged section B is unlikely to be restricted. Therefore, the projection length t0 of the rubber plug 60 protruding from the outer tube 46 is less as compared to a comparative example (FIG. 6B). When the swaged section A begins to be swaged, rubber in the swaged section B acts so as to restrict the elongation of the rubber plug 60 due to the swaging of the swaged section A because the swaged section B has already begun to be swaged. Since only the swaged section B begins to be primarily swaged, the swaged section A begins to be swaged in such a state that the rubber plug 60 is axially aligned at the swaged section B. Therefore, though swaging proceeds, the elongation of the rubber plug 60 is absorbed by the portion, located between the swaged sections A and B, corresponding to the predetermined distance LS; hence, the projection length t of the rubber plug 60 protruding from the outer tube 46 can be reduced as compared to the comparative example (FIG. 6C). Thus, the misalignment of the rubber plug 60 due to swaging is reduced and therefore the rubber plug 60 after swaging can be kept at substantially the same position. Since the projection length t of the rubber plug 60 protruding from the outer tube 46 is reduced without varying the indentation depth during swaging as described above, the pressure in the rubber plug 60 in the outer tube 46 can be increased. Therefore, sealing properties of the rubber plug 60 can be maintained for a long period. Since the position of the rubber plug 60 is not significantly varied before and after swaging (misalignment is reduced and substantially the same position is kept), the axial force (tensile force) applied to the leads 48 and the connections 52a during swaging is reduced and therefore the breakage of the leads 48 and the failure of the connections 52a can be prevented from occurring. These are the reasons why the swaged section B begins to be primarily swaged during swaging.

The correspondence between elements of this embodiment and elements of the present invention is described below. The sensor element 20 corresponds to a "sensor element" of the present invention, the connector 50 corresponds to a "connector" of the present invention, the outer tube 46 corresponds to a "tubular body" of the present invention, the leads 48 correspond to "leads" of the present invention, the rubber plug 60 corresponds to an "elastic body" of the present invention, the swaged section A corresponds to a "first swaged section" of the present invention, and the swaged section B corresponds to a "second swaged section" of the present invention.

According to this embodiment, the outer tube 46 and the rubber plug 60 are swaged at two sites, that is, the swaged section A, which is located on the connections 52a, and the swaged section B, which is located on the open end 46a side of the outer tube 46, such that the inside diameter φA of the portion of the rubber plug 60 that corresponds to the swaged section A is greater than the inside diameter φB of the portion of the rubber plug 60 that corresponds to the swaged section B. Therefore, the swaged section B is more heavily swaged than the swaged section A, whereby sealing properties are ensured and leakage can be prevented. The swaged section A is more lightly swaged than the swaged section B, whereby the failure of the connections 52a and the like can be prevented. In the swaged section B, the swaging ratio is set within the range of 8% to 14% and therefore sealing properties can be reliably ensured. Furthermore, in the swaged section A, the swaged section A is set to be 1% to 5% greater than the swaged section B; hence, the swaged section A is more lightly swaged than the swaged section B and sealing properties can be prevented from being significantly impaired. Since the rubber plug 60 contains the filler, sealing properties can be maintained for a long period by increasing the pressure in the rubber plug 60. These allow better sealing properties and electrical connectivity to be ensured.

According to this embodiment, in swaging, among the two swaged sections A and B, the swaged section B begins to be primarily swaged; hence, strong force can be prevented from acting on the rubber plug 60 in a free state at a time and the swaged section A can begin to be swaged in such a state that the portion of the rubber plug 60 that corresponds to the swaged section B is aligned as compared to the case where the swaged sections A and B begin to be simultaneously swaged. Therefore, the position of the rubber plug 60 can be prevented from being significantly varied and the rubber plug 60 can be prevented from protruding from the outer tube 46; hence, the breakage of the leads 48 and the failure of the connections 52a can be prevented from occurring and sealing properties can be maintained for a long period by increasing the pressure in the rubber plug 60. In addition, the elongation of the rubber plug 60 can be absorbed by the portion, located between the swaged sections A and B, corresponding to the predetermined distance LS and therefore the pressure in the rubber plug 60 can be further increased.

The present invention is not limited to this embodiment and various modifications can be made within the technical scope of the present invention.

In this embodiment, the swaged section A is a site corresponding to the connections 52a and the swaging width LA of the swaged section A is within the width of the connections 52a. Instead, the width of the connections 52a may be within the swaging width LA of the swaged section A or the swaging width LA of the swaged section A may partly overlap the width of the connections 52a.

In this embodiment, the two swaged sections A and B are swaged. Instead, three or more sites may be swaged. In the case of swaging three or more sites, it is only necessary that the inside diameter φA of the swaged section A, which is the site corresponding to the connections 52a, is greater than the inside diameter φA of a swaged section other than the swaged section A. In a step of swaging three or more sites, it is only necessary that a swaged section other than the swaged section A begins to be primarily swaged.

In this embodiment, in swaging, the swaged section B begins to be primarily swaged. Instead, the swaged section A may begin to be primarily swaged or the swaged sections A and B may begin to be simultaneously swaged. However, in order to prevent the position of the rubber plug 60 from being significantly varied and/or in order to reduce the projection length t of the rubber plug 60 protruding from the outer tube 46 as described above, the swaged section B preferably begins to be primarily swaged as described in this embodiment.

In this embodiment, the swaged section A begins to be swaged in the course of swaging the swaged section B. Instead, after the swaged section B is swaged, the swaged section A may begin to be swaged.

In this embodiment, the rubber plug 60 is the member made of fluoro-rubber. Instead, the rubber plug 60 may be made of another material, such as a heat-resistant resin, capable of sealing the open end 46a of the outer tube 46.

In this embodiment, the rubber plug 60 contains the filler. Instead, the rubber plug 60 need not contain the filler.

In this embodiment, the swaged sections A and B are swaged with the swaging tools 102 common thereto. Instead, the swaged sections A and B may be separately swaged with separate swaging tools.

In this embodiment, the height ha of the bumps 102a of the swaging tools 102 is different from the height hb of the bumps 102b thereof. Instead, the height ha of the bumps 102a may be the same as the height hb of the bumps 102b and the swaging tools 102 may be different in indentation depth from each other.

In this embodiment, the predetermined distance LS is present between the swaged sections A and B. Instead, the swaged sections A and B may be stepwise connected with no distance therebetween.

In this embodiment, the swaging width LA of the swaged section A is the same as the swaging width LB of the swaged section B. Instead, the swaging width LA of the swaged section A may be different from the swaging width LB of the swaged section B. For example, the swaging width LB of the swaged section B may be greater than the swaging width LA of the swaged section A. This allows sealing properties to be further ensured and leakage to be further prevented because the swaging width LB of the swaged section B is large and also allows excessive force to be prevented from acting on the connections 52a because the swaging width LA of the swaged section A is small.

EXAMPLES

Preliminary Test

Before the gas sensor 10 shown in FIG. 10 was manufactured, the following test was carried out: a preliminary test to determine the range of the swaging ratio of the inside diameter φB as the reference inside diameter of the swaged outer tube 46. In the preliminary test, the following sensors were prepared: gas sensors subjected to single-stage swaging at a single swaged section and gas sensors subjected to two-stage swaging at two swaged sections. In the preliminary test, unlike the above embodiment, the gas sensors were swaged so as to have the same inside diameter. Seven of the gas sensors subjected to single-stage swaging and seven of the gas sensors subjected to two-stage swaging were prepared and were swaged such that the inside diameter before swaging was reduced from 11.8 mm to 11.0 mm (about 7%), 10.8 mm (about 8%), 10.6 mm (about 10%), 10.4 mm (about 12%), 10.2 mm (about 14%), 10.0 mm (about 15%), or 9.8 mm (about 17%) by swaging (each parenthesized value is the swaging ratio). The outside diameter of the unswaged rubber plug 60 was 11.0 mm. In the preliminary test, each prepared gas sensor was attached to a gas pipe similar to an automotive exhaust pipe. As shown in heating conditions in Table 1, a heating test was continuously carried out for 100 hours in such a way that the rubber plug 60 is exposed to high temperature, about 250° C., by introducing about 850° C. gas into the gas pipe using a gas burner. After the heating test was finished, a leakage test to check the leakage of air was carried out in such a way that air with a static pressure of 0.1 MPa was applied to the gas sensor from the lead 48 side. Subsequently, the rubber plug 60 was taken out of the gas sensor and was checked for the presence of cracks, whereby the rubber plug 60 was evaluated for durability.

TABLE 1

| HEATING DEVICE | $C_3H_8$ BURNER |
| --- | --- |
| GAS TEMPERATURE | 850° C. |
| RUBBER PLUG TEMPERATURE | 250° C. |
| HEATING TIME | 100 hours |

Table 2 shows results of the preliminary test. In the leakage test, the gas sensors, subjected to single-stage swaging, having an inside diameter φB of 10.6 mm to 11.0 mm had leaks and those having an inside diameter φB of 9.8 mm to 10.4 mm had no leaks. In Table 2, the symbol "B" denotes the absence of leaks and the symbol "D" denotes the presence of leaks problematic in practical use. The gas sensor, subjected to two-stage swaging, having an inside diameter φB of 11.0 mm had leaks and the others having an inside diameter φB of 9.8 mm to 10.8 mm had no leaks. In the evaluation of durability, the gas sensors, subjected to single- or two-stage swaging, having an inside diameter φB of 10.2 mm to 11.0 mm had no cracks (denoted by "B") and were good in durability. However, those having an inside diameter φB of 9.8 mm or 10.0 mm had cracks (denoted by "D") and were poor in durability.

TABLE 2

| | | LEAKAGE TEST | | DURABILITY OF RUBBER PLUG | |
| --- | --- | --- | --- | --- | --- |
| REFERENCE INSIDE DIAMETER φB(mm) | SWAGING RATIO | SINGLE-STAGE SWAGING | TWO-STAGE SWAGING (TWO-STAGE WITH SAME INSIDE DIAMETER) | SINGLE-STAGE SWAGING | TWO-STAGE SWAGING (TWO-STAGE WITH SAME INSIDE DIAMETER) |
| φ11.0 | 7% | D | D | B | B |
| φ10.8 | 8% | D | B | B | B |
| φ10.6 | 10% | D | B | B | B |
| φ10.4 | 12% | B | B | B | B |
| φ10.2 | 14% | B | B | B | B |
| φ10.0 | 15% | B | B | D | D |
| φ9.8 | 17% | B | B | D | D |

The results of the preliminary test indicate the following. First, the reference inside diameter (inside diameter φB) capable of preventing leakage and keeping durability is preferably within the range of 10.2 mm to 10.8 mm, that is, the swaging ratio is preferably within the range of 8% to 14%. In the above embodiment, the inside diameter φA is greater than the inside diameter φB; hence, one having a high leakage prevention effect only by a single stage of the inside diameter φB is required. Therefore, the inside diameter φB is more preferably within the range of 10.2 mm to 10.4 mm, that is, the swaging ratio is more preferably within the range of 12% to 14%.

Evaluation Test 1

For the inside diameter φB determined as the reference inside diameter in the preliminary test, gas sensors for comparative examples in which the inside diameter φA was determined at an inside diameter variance of 0% (the same diameter) and gas sensors for examples in which the inside diameter φA was determined at an inside diameter variance within a predetermined range were prepared, followed by Evaluation Test 1. In the preliminary test, the preferred range of the inside diameter φB was 10.2 mm to 10.8 mm; hence, three sizes, 10.8 mm, 10.4 mm, and 10.2 mm, were used as values of the inside diameter φB. The inside diameter variance of the examples was within the range of 0.1% to 7% and was set to 0.1%, 0.5%, 1%, 2%, 3%, 4%, 5%, 6%, or 7%. In Evaluation Test 1, a heating test was carried out in substantially the same manner as that described in the preliminary test. After the heating test was finished, the above leakage test was carried out. Subsequently, the elongation ΔL of the whole rubber plug 60 was investigated. As the elongation ΔL of the whole rubber plug 60 as well as the projection length t of the rubber plug 60 increases, the tensile force acting on the leads 48 increases; hence, connection failure or disconnection is likely to occur and therefore electrical connectivity is reduced in some cases. The increase in elongation ΔL of the rubber plug 60 leads to the reduction of sealing properties because the pressure in the rubber plug 60 is reduced. Herein, it has been grasped that in the rubber plug 60 having an outside diameter of 11.0 mm and a length L of 14.5 mm in an initial state before swaging, electrical connectivity or sealing properties are affected in some cases when the elongation ΔL is 2.5 mm or more and such influence is significant when the elongation ΔL is 3.0 mm or more. Therefore, an elongation ΔL of less than 2.5 mm was rated as "B", an elongation ΔL of 2.5 mm to less than 3.0 mm was rated as "C", and an elongation ΔL of 3.0 mm or more was rated as "D". In the manufacture of the gas sensor 10, the projection length t of the rubber plug 60 protruding from the outer tube 46 is preferably about 1 mm and is aimed at the range of 1 mm plus/minus 0.5 mm (the range of a lower limit of 0.5 mm to an upper limit of 1.5 mm).

Table 3 shows results of Experimental Examples 1 to 10 in the case of an inside diameter φB of 10.8 mm. Experimental Example 1 corresponds to a comparative example and Experimental Example 2 to 10 correspond to examples. In the leakage test, Experimental Example 1 to 8 (an inside diameter variance of 0% or 0.1% to 5%) had no leaks and were rated as "B" and Experimental Examples 9 and 10 (an inside diameter variance of 6% or 7%) had slight leaks and were rated as "C". In results of the leakage test, the symbol "B" denotes the absence of leaks as described above and the symbol "C" denotes the presence of slight leaks not problematic in practical use. For the elongation ΔL of the whole rubber plug 60, Experimental Example 1 (an inside diameter variance of 0%) exhibited 2.5 mm and was rated as "C" and Experimental Examples 2 to 10 (an inside diameter variance of 0.1% to 7%) exhibited less than 2.5 mm and were rated as "B". Therefore, for comprehensive evaluation in the case of an inside diameter φB of 10.8 mm, Experimental Examples 2 to 8 (an inside diameter variance of 0.1% to 5%) were rated as "A" and Experimental Examples 1, 9, and 10 were rated as "B". For comprehensive evaluation, the symbol "A" denotes that both the leakage test and the elongation ΔL are rated as "B", the symbol "B" denotes that one of the leakage test and the elongation ΔL is rated as "B" and the other is rated as "C", and the symbol "D" denotes that one of the leakage test and the elongation ΔL is rated as "D".

TABLE 3

| INSIDE DIAMETER VARIANCE | REFERENCE INSIDE DIAMETER φB: 10.8 mm | | LEAKAGE TEST | ELONGATION ΔL | COMPREHENSIVE EVALUATION |
|---|---|---|---|---|---|
| 0% | EXPERIMENTAL EXAMPLE 1 | φA: 10.8 mm | B | 2.5 mm(Δ) | B |
| 0.1% | EXPERIMENTAL EXAMPLE 2 | φA: 10.81 mm | B | 2.0 mm(○) | A |
| 0.5% | EXPERIMENTAL EXAMPLE 3 | φA: 10.85 mm | B | 1.9 mm(○) | A |
| 1% | EXPERIMENTAL EXAMPLE 4 | φA: 10.91 mm | B | 1.8 mm(○) | A |
| 2% | EXPERIMENTAL EXAMPLE 5 | φA: 11.02 mm | B | 1.6 mm(○) | A |
| 3% | EXPERIMENTAL EXAMPLE 6 | φA: 11.12 mm | B | 1.4 mm(○) | A |
| 4% | EXPERIMENTAL EXAMPLE 7 | φA: 11.23 mm | B | 1.3 mm(○) | A |
| 5% | EXPERIMENTAL EXAMPLE 8 | φA: 11.34 mm | B | 1.1 mm(○) | A |
| 6% | EXPERIMENTAL EXAMPLE 9 | φA: 11.45 mm | C | 1.0 mm(○) | B |
| 7% | EXPERIMENTAL EXAMPLE 10 | φA: 11.56 mm | C | 0.8 mm(○) | B |

Table 4 shows results of Experimental Examples 11 to 20 in the case of an inside diameter φB of 10.4 mm. Experimental Example 11 corresponds to a comparative example and Experimental Examples 12 to 20 correspond to examples. In the leakage test, Experimental Examples 11 to 19 (an inside diameter variance of 0% or 0.1% to 6%) had no leaks and were rated as "B" and Experimental Example 20 (an inside diameter variance of 7%) had slight leaks and were rated as "C". For the elongation ΔL of the whole rubber plug 60, Experimental Example 11 (an inside diameter variance of 0%) exhibited 3.5 mm and was rated as "D", Experimental Example 12 (an inside diameter variance of 0.1%) exhibited 2.5 mm and was rated as "C", and Experimental Examples 13 to 20 (an inside diameter variance of 0.5% to 7%) exhibited less than 2.5 mm and were rated as "B". Therefore, for comprehensive evaluation in the case of an inside diameter φB of 10.4 mm, Experimental Examples 13 to 19 (an inside diameter variance of 0.5% to 6%) were rated as "A", Experimental Examples 12 and 20 (an inside diameter variance of 0.1% or 7%) were rated as "B", and Experimental Example 11 (an inside diameter variance of 0%) was rated as "D".

TABLE 4

| INSIDE DIAMETER VARIANCE | REFERENCE INSIDE DIAMETER φB: 10.4 mm | | LEAKAGE TEST | ELONGATION ΔL | COMPREHENSIVE EVALUATION |
|---|---|---|---|---|---|
| 0% | EXPERIMENTAL EXAMPLE 11 | φA: 10.4 mm | B | 3.5 mm(x) | D |
| 0.1% | EXPERIMENTAL EXAMPLE 12 | φA: 10.41 mm | B | 2.5 mm(Δ) | B |
| 0.5% | EXPERIMENTAL EXAMPLE 13 | φA: 10.45 mm | B | 2.2 mm(○) | A |

TABLE 4-continued

| INSIDE DIAMETER VARIANCE | REFERENCE INSIDE DIAMETER φB: 10.4 mm | | LEAKAGE TEST | ELONGATION ΔL | COMPREHENSIVE EVALUATION |
|---|---|---|---|---|---|
| 1% | EXPERIMENTAL EXAMPLE 14 | φA: 10.50 mm | B | 2.0 mm(○) | A |
| 2% | EXPERIMENTAL EXAMPLE 15 | φA: 10.61 mm | B | 1.8 mm(○) | A |
| 3% | EXPERIMENTAL EXAMPLE 16 | φA: 10.71 mm | B | 1.6 mm(○) | A |
| 4% | EXPERIMENTAL EXAMPLE 17 | φA: 10.82 mm | B | 1.4 mm(○) | A |
| 5% | EXPERIMENTAL EXAMPLE 18 | φA: 10.92 mm | B | 1.2 mm(○) | A |
| 6% | EXPERIMENTAL EXAMPLE 19 | φA: 11.02 mm | B | 1.1 mm(○) | A |
| 7% | EXPERIMENTAL EXAMPLE 20 | φA: 11.13 mm | C | 1.0 mm(○) | B |

Table 5 shows results of Experimental Examples 21 to 30 in the case of an inside diameter φB of 10.2 mm. Experimental Example 21 corresponds to a comparative example and Experimental Examples 22 to 30 correspond to examples. In the leakage test, all of Experimental Examples 21 to 30 (an inside diameter variance of 0% or 0.1% to 7%) had no leaks and were rated as "B". For the elongation ΔL of the whole rubber plug 60, Experimental Example 21 (an inside diameter variance of 0%) exhibited 4.0 mm and was rated as "D", Experimental Examples 22 and 23 (an inside diameter variance of 0.1% or 0.5%) exhibited 2.5 mm to less than 3.0 mm and were rated as "C", and Experimental Examples 24 to 30 (an inside diameter variance of 1% to 7%) exhibited less than 2.5 mm and were rated as "B". Therefore, for comprehensive evaluation in the case of an inside diameter φB of 10.2 mm, Experimental Examples 24 to 30 (an inside diameter variance of 1% to 7%) were rated as "A", Experimental Examples 22 and 23 (an inside diameter variance of 0.1% or 0.5%) were rated as "B", and Experimental Example 21 was rated as "D".

The above results of the preliminary test and Evaluation Test 1 indicate that for the inside diameter φB, the swaging ratio is preferably within the range of 8% to 14% (the range of 10.2 mm to 10.8 mm) and more preferably within the range of 12% to 14% (the range of 10.2 mm to 10.4 mm). The inside diameter variance determined by dividing the difference between the inside diameter φA and the inside diameter φB by the inside diameter φB is preferably within the range of 1% to 5%. Therefore, as an example of the size of a swaged section in an example, it is conceivable that the inside diameter φB is adjusted to 10.4 mm within the range of 10.2 mm and 10.4 mm and the inside diameter variance is adjusted to 2% in the range of 1% to 5%. That is, the inside diameter φB was adjusted to 10.4 mm, the inside diameter variance was adjusted to 2% with respect to an inside diameter φB of 10.4 mm, and the inside diameter φA was adjusted to 10.6 mm. Furthermore, the swaging width LA and the swaging width LB were both adjusted to 2.5 mm and the swaging distance LS was adjusted to 3.5 mm.

TABLE 5

| INSIDE DIAMETER VARIANCE | REFERENCE INSIDE DIAMETER φB: 10.2 mm | | LEAKAGE TEST | ELONGATION ΔL | COMPREHENSIVE EVALUATION |
|---|---|---|---|---|---|
| 0% | EXPERIMENTAL EXAMPLE 21 | φA: 10.2 mm | B | 4.0 mm(x) | D |
| 0.1% | EXPERIMENTAL EXAMPLE 22 | φA: 10.21 mm | B | 2.8 mm(○) | B |
| 0.5% | EXPERIMENTAL EXAMPLE 23 | φA: 10.25 mm | B | 2.6 mm(○) | B |
| 1% | EXPERIMENTAL EXAMPLE 24 | φA: 10.30 mm | B | 2.4 mm(○) | A |
| 2% | EXPERIMENTAL EXAMPLE 25 | φA: 10.40 mm | B | 2.0 mm(○) | A |
| 3% | EXPERIMENTAL EXAMPLE 26 | φA: 10.51 mm | B | 1.9 mm(○) | A |
| 4% | EXPERIMENTAL EXAMPLE 27 | φA: 10.61 mm | B | 1.8 mm(○) | A |
| 5% | EXPERIMENTAL EXAMPLE 28 | φA: 10.71 mm | B | 1.5 mm(○) | A |
| 6% | EXPERIMENTAL EXAMPLE 29 | φA: 11.81 mm | B | 1.3 mm(○) | A |
| 7% | EXPERIMENTAL EXAMPLE 30 | φA: 11.91 mm | B | 1.1 mm(○) | A |

The results of Evaluation Test 1 indicate the following. Comparative examples (Experimental Examples 1, 11, and 21) with an inside diameter variance of 0% were rated as "B" in the case of an inside diameter φB of 10.8 mm or were rated as "D" in the case of an inside diameter φB of 10.4 mm or 10.2 mm because the elongation ΔL of the whole rubber plug 60 was large. Therefore, it is conceivable that an inside diameter variance of 0% adversely affects electrical connectivity with relatively high probability. On the other hand, examples (Experimental Examples 2 to 10, 12 to 20, and 22 to 30) with an inside diameter variance of 0.1% to 7% were all rated as "A" or "B". Therefore, in these examples, leaks and the reduction of electrical connectivity can be well prevented. In particular, examples (Experimental Examples 4 to 8, 14 to 18, and 24 to 28) with an inside diameter variance of 1% to 5% were all rated as "A". That is, in the examples with an inside diameter variance of 1% to 5%, leaks and the reduction of electrical connectivity can be further well prevented regardless of the value of the inside diameter φB.

Evaluation Test 2

Thirty gas sensors 10 including swaged sections having a size determined as described above were manufactured by a method in which a the swaged section B begins to be swaged prior to the swaged section A as described in the above embodiment, followed by measuring the projection length t of each rubber plug 60. Table 6 shows the measurement results. The projection length t ranged from 0.84 mm at minimum to 1.19 mm at maximum and was 1.04 mm on average. The projection length t was within the range of 1.0±0.5 mm, which is a target value as described above. This result was better than a result obtained by allowing the swaged sections A and B to begin to be simultaneously swaged. Therefore, in the gas sensors 10 manufactured by the method described in the above embodiment, the effect of preventing leaks and the effect of preventing the reduction of electrical connectivity are high.

TABLE 6

| No. | PROJECTION LENGTH t(mm) |
|---|---|
| 1 | 1.19 |
| 2 | 0.84 |
| 3 | 1.08 |
| 4 | 0.91 |
| 5 | 0.89 |
| 6 | 0.99 |
| 7 | 1.12 |
| 8 | 1.00 |
| 9 | 1.05 |
| 10 | 1.10 |
| 11 | 1.05 |
| 12 | 1.13 |
| 13 | 1.06 |
| 14 | 0.98 |
| 15 | 1.02 |
| 16 | 1.14 |
| 17 | 0.89 |
| 18 | 0.92 |
| 19 | 1.03 |
| 20 | 1.11 |
| 21 | 1.06 |
| 22 | 1.16 |
| 23 | 1.16 |
| 24 | 1.10 |
| 25 | 1.05 |
| 26 | 1.00 |
| 27 | 1.12 |
| 28 | 0.98 |
| 29 | 1.10 |
| 30 | 1.02 |
| MAX | 1.19 |
| MIN | 0.84 |
| AVE | 1.04 |

What is claimed is:

1. A gas sensor comprising:
a sensor element configured to detect a concentration of measured gas;
a connector electrically connected to the sensor element;
a tubular body having the sensor element and the connector disposed therein, and having an open end;
a plurality of leads connected to the connector and extending outward from the open end of the tubular body; and
an elastic body disposed in the tubular body so as to seal the open end, having connections between the connector and the leads disposed therein, and having the plurality of leads extend therethrough,
the tubular body and the elastic body being radially swaged at a plurality of swaged sections including a first swaged section disposed on the connection side and a second swaged section disposed closer to the open end than the first swaged section, and
a portion of the tubular body having an inside diameter corresponding to the first swaged section greater than an inside diameter of a portion of the tubular body corresponding to the second swaged section.

2. The gas sensor according to claim 1,
wherein
the inside diameter of the portion of the tubular body corresponding to the first swaged section is 1% to 5% greater than the inside diameter of the portion of the tubular body corresponding to the second swaged section.

3. The gas sensor according to claim 1,
wherein
a swaging ratio determined by dividing the difference in the inside diameter between the portion of the tubular body before swaging corresponding to the second swaged section and the portion of the tubular body after swaging corresponding to the second swaged section by the inside diameter of the tubular body before swaging is within the range of 8% to 14%.

4. The gas sensor according to claim 1,
wherein
the elastic body includes an inorganic filler.

* * * * *